United States Patent
Buchwald et al.

(10) Patent No.: US 8,105,247 B2
(45) Date of Patent: Jan. 31, 2012

(54) DEVICE FOR MONITORING SIZE OF LUMINAL CAVITY

(75) Inventors: Henry Buchwald, Edina, MN (US); Thomas J. O'Dea, Shoreview, MN (US)

(73) Assignee: Buchwald O'Dea LLC, Edina, MN (US)

(*) Notice: Subject to any disclaimer, the term of this patent is extended or adjusted under 35 U.S.C. 154(b) by 301 days.

(21) Appl. No.: 12/179,927

(22) Filed: Jul. 25, 2008

(65) Prior Publication Data

US 2010/0022853 A1   Jan. 28, 2010

(51) Int. Cl.
*A61B 5/103*   (2006.01)
*A61B 5/117*   (2006.01)

(52) U.S. Cl. .................................. 600/593; 600/587

(58) Field of Classification Search .......... 600/300, 600/301, 407, 409, 411, 419, 421, 422, 423, 600/546, 547, 560, 561, 587, 593, 595, 29, 600/30, 31; 606/151, 157, 139
See application file for complete search history.

(56) References Cited

U.S. PATENT DOCUMENTS

| | | | |
|---|---|---|---|
| 5,938,669 | A | 8/1999 | Klaiber et al. |
| 6,210,347 | B1 | 4/2001 | Forsell |
| 6,676,674 | B1 | 1/2004 | Dudai |
| 7,328,070 | B2 | 2/2008 | Gerber et al. |
| 7,338,433 | B2 | 3/2008 | Coe |
| 2005/0073310 | A1 | 4/2005 | Weatherall et al. |
| 2007/0010238 | A1 | 1/2007 | Wlckham |
| 2008/0009680 | A1 | 1/2008 | Hassler, Jr. |
| 2008/0097188 | A1 | 4/2008 | Pool et al. |

*Primary Examiner* — Jeffrey G Hoekstra
(74) *Attorney, Agent, or Firm* — Vidas, Arrett & Steinkraus

(57) ABSTRACT

A system for measuring the size of a gastric lumen includes a gastric banding device, an antenna positioned outside of the patient's body, and a receiver in operative communication with the antenna. The banding device comprises two orthogonal ultrasonic transceiver modules, a microprocessor, and a transmitter in electrical communication with the microprocessor. The microprocessor is in operative communication with each of the two transceiver modules. The transmitter transmits signals to a receiver positioned outside of a patient's body. Another system for measuring the size of a gastric lumen includes a gastric banding device having a first coiled conductor. The system further comprises a circuit external to the banding device, the circuit comprising a second coiled conductor. The circuit further comprises a tunable frequency generator and a spectrum analyzer, the circuit being tunable to allow a resonant frequency.

11 Claims, 10 Drawing Sheets

DEVICE FOR MONITORING SIZE OF LUMINAL CAVITY

CROSS-REFERENCE TO RELATED APPLICATIONS

Not Applicable

STATEMENT REGARDING FEDERALLY SPONSORED RESEARCH

Not Applicable

FIELD OF THE INVENTION

In some embodiments this invention relates to an adjustable gastric band to treat obesity. Some embodiments are directed to methods of adjusting the size of an implanted adjustable gastric band. Other embodiments relate to luminal dimensions assessments in humans, as well as in inanimate conduits or devices.

BACKGROUND OF THE INVENTION

At the turn of the $21^{st}$ century, obesity is the epidemic with the greatest prevalence and incidence in the United States. Obesity is defined as having a body mass index (BMI)$\geqq 30$ kg/m$^2$, and morbid obesity, or clinically severe obesity, is defined as having a BMI$\leqq 40$ kg/m$^2$, or a BMI$\leqq 35$ kg/m$^2$ with co-existing comorbid conditions. It is estimated that there are approximately 20 million people in the United States who are morbidly obese.

Obesity is not primarily a cosmetic problem. Obesity and morbid obesity are associated with: hypertension; atherosclerotic cardiovascular disease (coronary, cerebral, and peripheral); hypercholesterolemia; type 2 diabetes; asthma; obstructive sleep apnea; gallstones; cirrhosis and carcinoma of the liver; carcinoma of breast and uterus; low-back syndrome and herniated disks; weight bearing osteoarthritis of the hips, knees, ankles, and feet; lower extremity edema and varicosities; thrombophlebitis and pulmonary emboli; skin fold rashes; and many other diseases. Furthermore, in our society, the obese and morbidly obese have psychological, social, marital, and sexual problems. Obesity is also an economic problem associated with denial of employment, restriction of career advancement and higher educational opportunities, and uninsurability or high insurance premiums.

Unfortunately, medical diet and drug therapy today may not be as effective as desired with respect to obesity, and most certainly morbid obesity. This disease has, however, definitively been shown to respond to bariatric or obesity surgery.

Bariatric surgery can be divided by mechanisms of action into four categories: malabsorptive, malabsorptive/restrictive, restrictive, and other procedures and approaches. Adjustable gastric banding, laparoscopic or non-laparoscopic, is restrictive in intent. The restrictive procedures of bariatric surgery can be performed more rapidly and are more physiological than any of the other bariatric procedures, since, as a rule, no part of the gastrointestinal tract is resected, bypassed, or rerouted.

In the last few years, gastric banding has become a dominant force in bariatric surgery operative technology, and has fairly well displaced the stapled and banded gastroplasty. It is the most utilized bariatric procedure in Europe and Australia and, though still second to gastric bypass, is gaining in popularity in the United States.

Adjustable gastric band placement is usually performed laparoscopically but could be performed by open or endoscopic surgery. This intervention creates a restriction of the upper gastric lumen, effectively separating the gastric lumen into a small (approximately 15 ml) upper pouch and the remainder of the gastric lumen, the gastric remnant. The gastric band's constriction of the upper gastric lumen and, therefore, its ability to regulate gastric flow to control food intake, is a function of adjustable inflation of the lumen of the band via a catheter and a subcutaneous port. There are different and patented engineering concepts for the construction of the different adjustable gastric bands, the catheters and ports, and the filling techniques. To the best of the inventors' knowledge, there are no existing patents or disclosures for directly determining the lumen size, diameter, or volume enclosed by the gastric band in a patient and, thereby, determining the unrestricted flow path for luminal contents, i.e., food.

Weight loss success of adjustable gastric banding, to a major degree, resides in follow-up care after band placement. Follow-up care is primarily a function of obtaining, maintaining, or adjusting the gastric lumen size of the gastric pathway through the constricting band. Optimal gastric lumen size provides for food restriction in comfortable balance with food intake, leading to a hypocaloric state and weight loss. To achieve this state, it is necessary to adjust the intraband fluid volume using the band's catheter and port or other mechanism.

This gastric lumen adjustment needs to take place up to or beyond six times per year, especially in the first year after band placement. The band volume adjustment is performed by a physician or a skilled nurse guided by the patient's subjective sensations of fullness or discomfort; expensive, radioactive exposure to x-rays and/or fluoroscopy; or newer technology equating intraband pressure with optimal gastric lumen size. None of these methods measures directly the gastric lumen size of the band and the size (diameter or volume) of the intragastric conduit within the encircling band. There is today no available technology directly to measure these parameters of gastric lumen size, and, thereby, determine the optimal adjustment of the intraband volume and constriction of the gastric lumen. Gastric band efficacy for each individual patient would be optimized if the gastric lumen size parameters could be directly measured. It may also be feasible to determine a formula or algorithm for gastric lumen size adjustment useable in adjustable gastric band patients as a class.

In summary, utilization of our method may allow for optimization of gastric lumen size adjustment and provide for comfortable weight loss with the adjustable gastric band, placed laparoscopically or nonlaparoscopically, and weight loss results beyond those achievable today, as well as enhanced patient satisfaction.

Gastric bands are described in U.S. Pat. Nos. 5,938,669, 6,210,347, 6,676,674, and 7,338,433, the entire contents of each being expressly incorporated herein by reference.

The art referred to and/or described above is not intended to constitute an admission that any patent, publication or other information referred to herein is "prior art" with respect to this invention.

All US patents and applications and all other published documents mentioned anywhere in this application are incorporated herein by reference in their entirety.

Without limiting the scope of the invention, a brief summary of some of the claimed embodiments of the invention is set forth below. Additional details of the summarized embodiments of the invention and/or additional embodiments of the invention may be found in the Detailed Description of the Invention below.

A brief abstract of the technical disclosure in the specification is provided for the purposes of complying with 37 C.F.R. §1.72.

BRIEF SUMMARY OF THE INVENTION

In at least one embodiment, the invention is directed to a system for measuring the size of a gastric lumen utilizing ultrasound. The system comprises a gastric banding device, an antenna positioned outside of the patient's body, and a receiver in operative communication with the antenna. The banding device comprises two orthogonal ultrasonic transceiver modules, a microprocessor, and a transmitter in electrical communication with the microprocessor. The microprocessor is in operative communication with each of the two transceiver modules. The transmitter is constructed and arranged for transmitting signals to a receiver positioned outside of a patient's body.

In some embodiments, the system comprises a gastric banding device having a first coiled conductor. The system further comprises a circuit external to the banding device, the circuit comprising a second coiled conductor. The circuit further comprises a tunable frequency generator and a spectrum analyzer, the circuit being tunable to allow a resonant frequency.

In at least one embodiment, the invention is directed to a method of measuring the size of a gastric lumen, the method comprising providing a system for measuring the size of a gastric lumen. The system comprises a gastric banding device having a first coiled conductor. The system further comprises a circuit external to the banding device, the circuit comprising a second coiled conductor. The circuit further comprises a tunable frequency generator and a spectrum analyzer, the circuit being tunable to allow a resonant frequency. The method further includes tuning the circuit external to the banding device to a first resonant frequency in the absence of a patient. The method further includes recording the first resonant frequency. The method further includes positioning the second coiled conductor near the patient. The method further includes providing a water solution for the patient to swallow. The method further includes tuning the circuit external to the banding device to a second resonant frequency in the presence of the patient. The method further includes calculating the size of the gastric lumen based on the difference between the first resonant frequency and the second resonant frequency.

In some embodiments, the present invention is directed towards a method of equipment verification using a gastric magnetic susceptibility phantom and system for measuring the size of a gastric lumen. The method comprises filling a peristaltic pump with a magnetic resonance imaging contrast material, the peristaltic pump having a longitudinal axis. The method further comprises disposing a first, second, and third gastric banding devices of claim 1 about the peristaltic pump, the first, second, and third banding devices being offset from one another along the longitudinal axis. The method further comprises setting the pump to a speed approximately equal to the speed of human swallowing. The method further comprises pumping the contrast material through the pump. The method further comprises positioning the second coiled conductor about the first banding device and determining the maximum deviation of the resonant frequency of the first banding device from the spectrum analyzer while contrast material is pumped through the pump. The method further comprises positioning the second coiled conductor about the second banding device and determining the resonant frequency of the second banding device from the spectrum analyzer while contrast material is pumped through the phantom. The method further comprises positioning the second coiled conductor about the third banding device and determining the resonant frequency of the third banding device from the spectrum analyzer while contrast material is pumped through the phantom. The method further comprises calculating the area of each of the first, second, and third bands based on their resonant frequencies.

These and other embodiments which characterize the invention are pointed out with particularity in the claims annexed hereto and forming a part hereof. However, for further understanding of the invention, its advantages and objectives obtained by its use, reference can be made to the drawings which form a further part hereof and the accompanying descriptive matter, in which there is illustrated and described an embodiments of the invention.

BRIEF DESCRIPTION OF THE SEVERAL VIEWS OF THE DRAWING(S)

A detailed description of the invention is hereafter described with specific reference being made to the drawings.

DETAILED DESCRIPTION OF THE INVENTION

Figure 1:
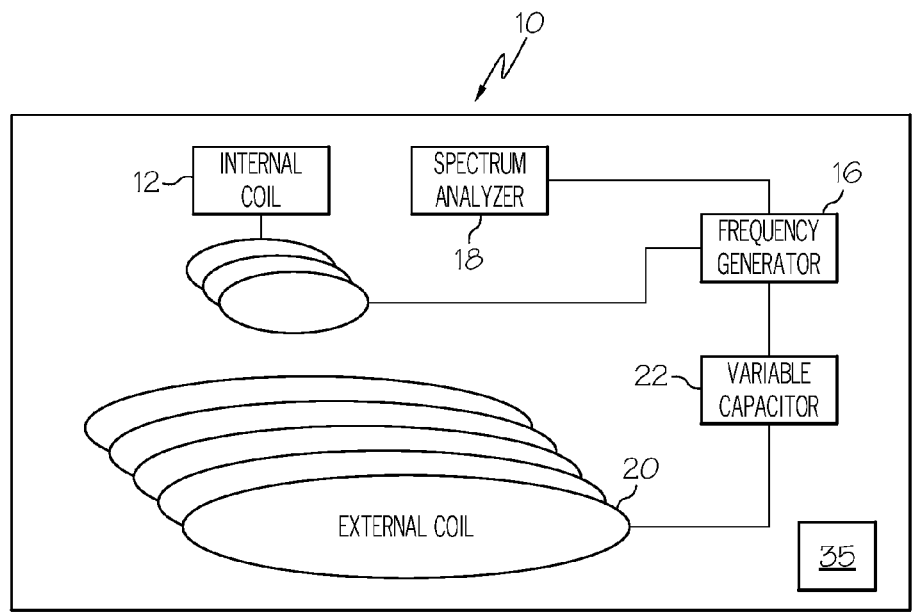
FIG. 1 is a schematic diagram depicting a system for measuring the size of a gastric lumen, in accordance with at least one embodiment of the present invention.

While this invention may be embodied in many different forms, there are described in detail herein specific embodiments of the invention. This description is an exemplification of the principles of the invention and is not intended to limit the invention to the particular embodiments illustrated.

For the purposes of this disclosure, like reference numerals in the figures shall refer to like features unless otherwise indicated.

Figure 2:
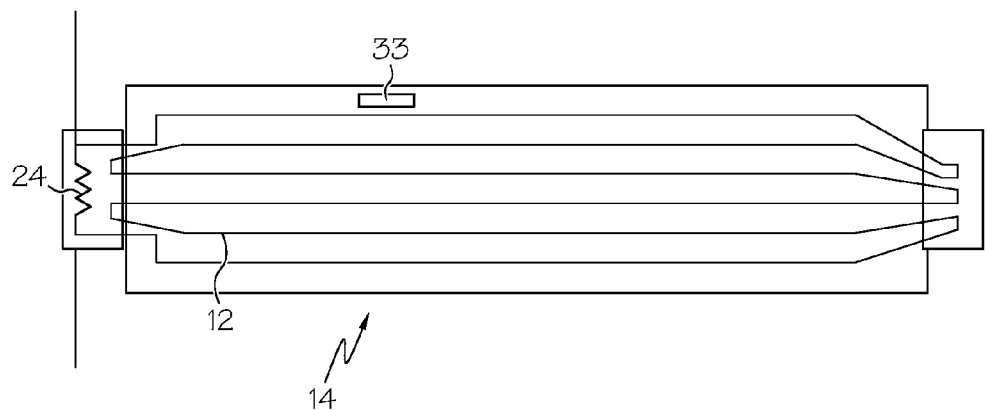
FIG. 2 is a schematic diagram of a laparoscopically adjustable gastric band with an internal coil, in accordance with at least one embodiment of the present invention.

Referring now to FIGS. 1 and 2, a system for measuring the size of a gastric lumen is illustrated in accordance with at least one embodiment of the present invention. The system 10 of FIG. 1 is used for measuring the size of the gastric lumen using an external tuned circuit and a passive coil embedded in a laparoscopically adjustable gastric band ("LAGB" or "lap band") gastric banding system. The system 10 includes a first coiled conductor 12 (or internal coil) positioned within a gastric banding device 14 (shown in more detail in FIG. 2). The phrases "internal coil" and "inner coil" are also used herein to denote the first coiled conductor 12. The system further includes a circuit external to the banding device and a patient that includes a tunable frequency generator 14, a spectrum analyzer 18, and a second coiled conductor 20. The phrases "external coil" and "outer coil" are also used herein to denote the second coiled conductor 20. The frequency generator may be a variable frequency oscillator, for example. The phrase "frequency generator" is used to denote any type of electrical or electronic device that produces repetitive electrical or electronic signals. For example, the frequency generator may be an electronic device capable of generating repeating sine waves. The phrase "spectrum analyzer" is used to denote any electrical or electronic device capable of measuring the frequency and amplitude of a signal.

The system further includes appropriate capacitance, inductance, and resistance to allow resonance both when a patient is absent and when the patient is present, as will be described in detail below. For example, the system shown in FIG. 1 includes a variable capacitor 22 that can be tuned to achieve resonance. Rather than providing a variable capacitor, in some embodiments, the capacitor can be of fixed value and a variable inductor can be included.

The system 10 may also include a device 24 for controlling heating within the interior coil 12, shown in FIG. 2. As seen in FIG. 2, the device 24, for example a resistor, is in electrical communication with the internal coil. In some embodiments, two electrical leads attached to the two-terminal resistor can be extended out from the gastric banding device, thereby allowing a measurement to be taken. That is, the first terminal of the resistor can be in electrical communication with a first end of a first electrical lead, and the second terminal of the resistor can be in electrical communication with a first end of a second electrical lead. The second ends of the first and second electrical leads can extend outward, external to the gastric banding device.

Figure 3:
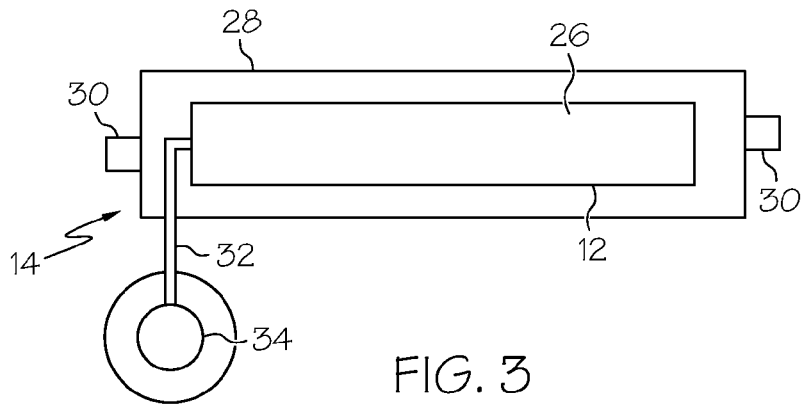
FIG. 3 is a schematic diagram of a laparoscopically adjustable gastric band with an internal coil, in accordance with at least one embodiment of the present invention.

In at least one embodiment, the electrical leads are accessible via an access port on the patient's body, as seen in FIG. 3. FIG. 3 depicts the LAGB 14 with internal coil 12, having an inflatable section 26, a solid substrate 28, and placement tabs 30. As seen, electrical leads 32 extend from the injection port 34 to the internal coil 12 to allow measurement of the current in the coil. In some embodiments, these leads can be conductively connected to the external circuit such that the external circuit includes the LAGB and its internal coil in the tuned circuit.

It should be noted that in the above-described embodiments, no battery or radiofrequency (RF) module is needed because the current in the lap band is a result of induction.

The system may further include a computer 35, depicted in FIG. 1, having software capable of performing calculations based on the current in the first coiled conductor and the resonant frequency in the external circuit in order to determine the size of the gastric lumen. The derivations, calculations, and theory of operation of the system are presented below.

Figure 4A:
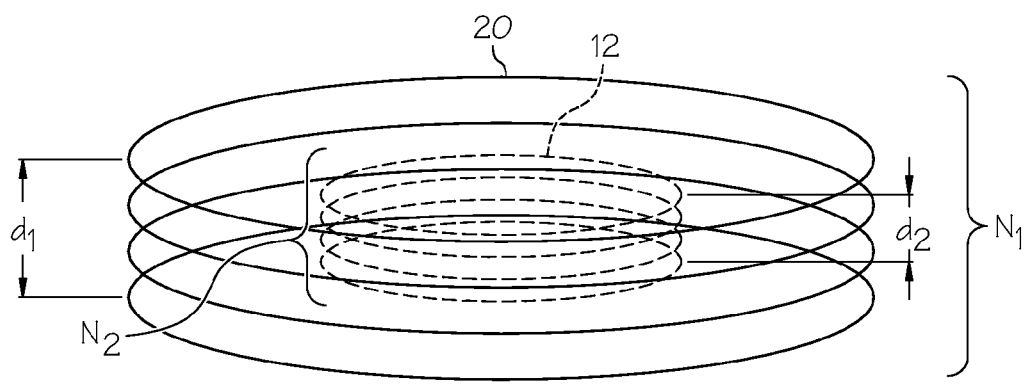
FIG. 4A is a schematic diagram depicting an inner coil and outer coil placed in a concentric coaxial arrangement.

Two embodiments of the present invention utilize induction to calculate the area of a gastric lumen. The first embodiment using induction to be considered is when the inner coil and the outer coil are placed concentrically and coaxially relative one another, as shown schematically in FIG. 4A. Such an embodiment occurs when the external coil is placed around the patient's body such that the inner coil in the LAGB is concentric with the external coil. The number of turns N of each solenoid is equal to the number of turns per unit length (n) * the length (d) of the solenoid. So, the number of turns of the outer solenoid in FIG. 4 is given by the equation $N_1 = n_1 * d_1$.

It is assumed that the external coil is excited with the following current:

$$I = I_0 \sin \omega t, \quad (1)$$

where $\omega$ = the angular frequency of the current source and $I_0$ is the maximum current of the current source. Then, the magnetic field B for a relatively long coil is given by the relation:

$$B = \mu \cdot N_1 I_0 \cdot \sin(\omega \cdot t)/d_1, \quad (2)$$

where $N_1$ is the number of turns in the coil, and $d_1$ is the length of the coil. The magnetic flux from the larger external coil subtended by the LAGB is:

$$\Phi = A_2 \cdot B = A_2 \cdot \mu \cdot N_1 \cdot I_0 \cdot \sin(\omega \cdot t)/d_1, \quad (3)$$

where $\mu$ is the magnetic susceptibility of the material contained within the area $A_2$ of the inner coil, B is the magnetic field density, and $N_1$ is the number of turns in the coil. The electromotive force (emf) generated by coil 1 in coil 2 is given by the relation:

$$E = -d\Phi/dt = -A_2 \cdot B = A_2 \mu \cdot N_1 \cdot \omega_1 \cdot I_0 \cdot (\cos \omega t)/d_1 \quad (4)$$

The voltage induced in the entire LAGB is given by the relation:

$$E_T = N_2 \cdot E = -A_2 \cdot \mu \cdot N_1 \cdot N_2 \cdot \omega_1 \cdot I_0 \cdot \cos(\omega \cdot t)/d_1 \quad (5)$$

The self inductance (L) of a coil is defined as:

$$L = N \cdot \Phi/i = N \cdot A \cdot \mu \cdot N/l = N^2 \cdot A \cdot \mu/d_1 \quad (6)$$

The self induced emf in the coil is then $$V = -L \, dI/dt = -\omega \cdot N^2 \cdot A \cdot \mu \cdot I_0 \cos(\omega \cdot t)/d_1 \quad (7)$$

The mutual inductance (M) of the two coils is defined as $$M_{21}=N_2 \cdot \Phi_{21} i_1, \tag{8}$$

where the current in coil 1 generates a flux in coil 2.

$$N_2 \cdot \Phi_{21}=N_2 \cdot B_1 \cdot \pi \cdot R_2^2, \tag{9}$$

and also $$N_2 \cdot \Phi_{21}=N_2 \cdot N_1 \cdot \pi \cdot \mu_0 \cdot R_2^2 \cdot i_1/2 \cdot R_1, \tag{10}$$

Thus the mutual inductance for the LAGB and the external coil can be given by $$M_{21}=N_2 \cdot N_1 \cdot \pi \cdot \mu_0 \cdot R_{2_1}^2/2 \cdot R_1 \tag{11}$$

It should be noted that although the magnetic field generated by the larger coil is essentially constant through the smaller coil, this is not true of the field induced by the smaller coil in the larger. But the mutual inductance of the larger coil upon the smaller is equal to that of the smaller coil upon the larger.

Continuing with the derivation, the voltage of a circuit is the sum of the voltages resulting from the resistance ($V_R$), capacitance ($V_C$), and inductance ($V_L$) such that $$V=V_R+V_C+V_L, \tag{12}$$

or as a function of time in integro-differential form, $$v(t)=I_1 \cdot R + L_1 \cdot dI_1/dt + 1/C \cdot \int I_1 dt, \tag{13}$$

or expressed completely as a differential equation:

$$\frac{1}{L_1} \cdot \frac{dv(t)}{dt} = \frac{d^2 I_1}{dt^2} + \frac{R}{L_1} \cdot \frac{dI_1}{dt} + \frac{1}{L_1 \cdot C} \cdot I_1. \tag{14}$$

If the variable frequency oscillator applies an excitation of $$v(t)=V_0 \sin(\omega t) \tag{15}$$

to the external coil and associated resistor and capacitor, then equation (14) can be written as $$\frac{V_0 \omega}{L_1} \cdot \frac{dv(t)}{dt} = \frac{d^2 I_1}{dt^2} + \left(\frac{1}{\tau_0}\right)\frac{dI_1}{dt} \cdot R + \omega_0^2 \cdot I_1, \text{ where} \tag{16}$$

$$\tau_0 = \frac{L_1}{R} \tag{17}$$

The tuned (or resonant) circuit including the external loop has a natural frequency given by:

$$\omega_n = \sqrt{1/(L \cdot C)} \tag{18}$$

The quality factor, or Q, of a resonant circuit is given by:

$$Q=\omega_n \cdot L/R = \sqrt{1/(L \cdot C)} \cdot L/R = 1/R \cdot \sqrt{L/C} \tag{19}$$

The bandwidth ($\omega_2 - \omega_1$) of the frequency plot (i.e. the width at half maximum response as measured by the spectrum analyzer) is given by:

$$\omega_2 - \omega_1 = \omega_n/Q = R/L_1 = 1/\tau_0 \tag{20}$$

If the induced emf in the LAGB coil is known, then $$V=N_2 \cdot A_2 \cdot B = A_2 \cdot \mu \cdot N_1 \cdot I_0 \cdot \omega/d_1 (\cos \omega t) \tag{21}$$

Considering the external tuned circuit without the LAGB included, then:

$$dV/dt = L \cdot d^2 I/dt^2 + R \cdot dI/dt + 1/C \cdot I, \tag{22}$$

which is the general equation for a series RLC circuit. So, $$1/L \cdot dV/dt = d^2 I/dt^2 + (1/\tau) \cdot dI/dt + \omega_0^2 \cdot I, \tag{23}$$

where $$\tau = L/R, \tag{24}$$

and $$\omega_n = \sqrt{1/(L \cdot C)} \tag{25}$$

The proportional half power frequencies are given by the relationship $$\Delta \omega_0/\omega_n = 1/2Q = 1/\tau \cdot \omega = R/L \cdot \sqrt{1/LC} = R \cdot \sqrt{C/L} \tag{26}$$

Now, an inductive circuit (which is a single conductive loop with no other resistance) is included in the external circuit that includes the LAGB. If the external coil is circuit 1 and the LAGB is circuit 2, then:

$$V_1 = L_1 \cdot d^2 I_1/dt^2 + M \cdot d^2 I_2/dt^2 + I_1 \cdot R_1 + 1/C \cdot \int I_1 \cdot dt \tag{27}$$

and because there applied voltage in the lap band, and because the resistance is small in the lap band, $$V_2 = 0 = L_2 \cdot d^2 I_2/dt^2 + M \cdot d^2 I_1/dt^2 \tag{28}$$

Because we observe only the current parameters in the external coil circuit, the current in the LAGB can be eliminated, leaving:

$$d^2 I_2/dt^2 = -M/L_2 \cdot d^2 I_1/dt^2, \tag{29}$$

then substituting into equation (27) gives $$V_1 = L_1 \cdot d^2 I_1/dt^2 + M \cdot -M/L_2 \cdot d^2 I_1/dt^2 + I_1 \cdot R_1 + 1/C \cdot \int I_1 \cdot dt. \tag{30}$$

Taking the derivative of equation (30):

$$\frac{dV}{dt} = \left(\frac{(L_1 \cdot L_2 - M^2)}{L^2}\right) \cdot \frac{d^2 I}{dt^2} + R \cdot \frac{dI}{dt} + 1/C \cdot I, \tag{31}$$

which equals $$\frac{L_2}{(L_1 \cdot L_2 - M^2)} \cdot \frac{dV}{dt} = \tag{32}$$

$$\frac{d^2 I_1}{dt^2} + \frac{R \cdot L_2}{(L_1 \cdot L_2 - M^2)} \cdot \frac{dI_1}{dt} \cdot \frac{L_2}{C \cdot (L_1 \cdot L_2 - M^2)} \cdot I_1,$$

which equals $$L_2/(L_1 \cdot L_2 - M^2) \cdot dV/dt = d^2 I/dt^2 + (1/\tau) \cdot dI/dt + \omega_0^2 \cdot I. \tag{33}$$

The resonance frequency of the external coil changes in the presence of the LAGB, as does the bandwidth of the frequency, as shown below:

$$\omega_0^2 = L_2/C \cdot (L_1 \cdot L_2 - M^2), \tag{34}$$

and where $$\tau = (L_1 \cdot L_2 - M^2)/R \cdot L_2 \tag{35}$$

Comparing the square of resonance frequency of the external coil in isolation and when concentric to the LAGB, the following ratio is obtained:

$$\frac{\omega_{no\_lap\_band}^2}{\omega_{lap\_band}^2} = \frac{\frac{1}{L_1} \cdot C}{\frac{L_2}{C \cdot (L_1 \cdot L_2 - M^2)}} \tag{36}$$

$$= \frac{(L_1 \cdot L_2 - M^2)}{(L_1 \cdot L_2)}$$

$$= 1 - \frac{M^2}{(L_1 \cdot L_2)}$$

where $\omega_{no\_lap\_band}$ is the natural frequency with no lap band coil in the circuit and $\omega_{lap\_band}$ is the natural frequency with the lap band coil in the circuit. Equation (36) assumes that the orientation of the external coil in relation to the LAGB is such that the resonance frequency is less in the presence of the LAGB. The ratio of the bandwidth is given by $$Q = \omega_n \cdot L/R = \sqrt{1/(L \cdot C)} \cdot L/R = 1/R\sqrt{L/C} \qquad (37)$$

The values of $L_1$, $L_2$, and M depend on the geometry of the coils. As stated above, the first embodiment is directed toward a configuration in which the inner coil and the outer coil are placed concentrically and coaxially, as in FIG. 4A. In such an embodiment, $$M = \pi \mu N_1 N_2 R_2^2 / 2R_1 = \mu N_1 N_2 A_2 / 2R_1, \qquad (38)$$

$$L_1 = N_1^2 \cdot A_1 \cdot \mu/d_1, \qquad (39)$$

and $$L_2 = N_2^2 \cdot A_2 \cdot \mu/d_2, \qquad (40)$$

where $R_1$ and $R_2$ are the radii of the two coils, $d_1$ and $d_2$ are the lengths of the two coils, and $A_1$ and $A_2$ are the respective areas enclosed by the coils.

Based on equations (38)-(40) for M, $L_1$, $L_2$, $$M^2/L_1L_2 = \pi \cdot \mu^2 \cdot N_1^2 \cdot N_2^2 \cdot A_2^2 \cdot d_1 \cdot d_2 / 4 \cdot N_1^2 \cdot N_2^2 \cdot A_1^2 \cdot A_2 \cdot \mu^2 = \pi \cdot A_2 \cdot d_1 \cdot d_2 / 4 \cdot A_1^2 \qquad (41)$$

Substituting into equation (36) results in $$\frac{\omega_{no\_lap\_band}^2}{\omega_{lap\_band}^2} = \frac{\frac{1}{L \cdot C}}{\frac{L_2}{C \cdot (L_1 \cdot L_2 - M^2)}} \qquad (42)$$

$$= \frac{(L_1 \cdot L_2 - M^2)}{(L_1 \cdot L_2)}$$

$$= 1 - \frac{\pi \cdot A_2 \cdot d_1 \cdot d_2}{4 \cdot A_1^2}$$

Solving for the area $A_2$ of the inner coil results in $$A_2 = \left(1 - \frac{\omega_{no\_lap\_band}^2}{\omega_{lap\_band}^2}\right) \cdot \left(\frac{4 \cdot A_1^2}{\pi \cdot d_1 \cdot d_2}\right) \qquad (43)$$

Figure 4B:
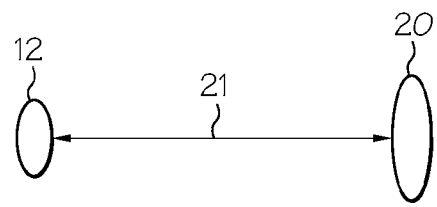
FIG. 4B is a schematic diagram depicting an inner coil and outer coil placed in a non-concentric coaxial arrangement.

The second embodiment using induction to be considered is when the inner coil 12 and the outer coil 20 are placed in a coaxial non-concentric arrangement relative to one another, as shown schematically in FIG. 4B. There is an impedance Z, shown at 21, between the coils. Such an embodiment occurs when the external coil is placed underneath or above, rather than around, the patient's body.

As stated earlier, the values of $L_1$, $L_2$, and M depend on the geometry of the coils. With the geometry of the second embodiment, namely of two coaxial non-concentric coils, $L_1$, $L_2$, and M are as follows:

$$M = \mu N_1 N_2 A_1 A_2 / 2\pi (R_1^2 + z^2)^{3/2}, \qquad (44)$$

and $$L_1 = N_1^2 \cdot A_1 \cdot \mu/d_1, \qquad (45)$$

and $$L_2 = N_2^2 \cdot A_2 \cdot \mu/d_2 \qquad (46)$$

Based on equations (44)-(46) for M, $L_1$, $L_2$, $$M^2/(L_1 \cdot L_2) = \mu^2 N_1^2 N_2^2 A_1^2 A_2^2 d_1 d_2 / 4_1 \pi^2 (R_1^2 + z^2)^3 N_1^2 N_2^2 A_1 A_2 \mu^2 = A_1 A_2 d_1 d_2 / 4\pi^2 (R_1^2 + z^2)^3 \qquad (47)$$

Substituting into equation (36) results in $$\frac{\omega_{no\_lap\_band}^2}{\omega_{lap\_band}^2} = \frac{\frac{1}{L \cdot C}}{\frac{L_2}{C \cdot (L_1 \cdot L_2 - M^2)}} \qquad (48)$$

$$= \frac{(L_1 \cdot L_2 - M^2)}{(L_1 \cdot L_2)}$$

$$= 1 - \frac{A_1 A_2 d_1 d_2}{4\pi^2 (R_1^2 + z^2)^3}$$

Solving for the area $A_2$ of the inner coil results in $$A_2 = \left(1 - \frac{\omega_{no\_lap\_band}^2}{\omega_{lap\_band}^2}\right) \cdot \left(\frac{4\pi^2 (R_1^2 + z^2)^3}{A_1 d_1 d_2}\right) \qquad (49)$$

The area of the concentric coaxial embodiment of equation (43) and the non-concentric coaxial embodiment of equation (49) can be summarized with the following equation:

$$A_2 = k \cdot \left(1 - \frac{\omega_{no\_lap\_band}^2}{\omega_{lap\_band}^2}\right), \qquad (50)$$

where k depends on the geometry of the coils. Thus, the area is proportional to the absolute value of one minus the ratio of the squares of the maximum resonant frequencies, as measured by the spectrum analyzer.

The effect of the LAGB coil on the external coil is given by $$\Delta\omega_0/\omega_n = 1/2Q = 1/\tau \cdot \omega \qquad (51)$$

Thus, the change in resonance frequency peak and the change in bandwidth can both be used to determine the product of the area and the magnetic susceptibility of the gastric lumen enclosed by the lap band. In both embodiments of the induction method, the external coil can be adjusted in both height and orientation relative to the LAGB coil to give maximum resonance frequency variation from isolation to insure proper relative position. The use of high magnetic susceptibility fluid in the lumen ensures that only the lumen area is measured rather than include the stomach tissue.

As stated earlier, the system may include a computer for calculating the area of the gastric lumen. A person of ordinary skill in the art would readily understand how to write software that calculates the area of the inner coil, as presented in equations (43) and (49) above, based on the foregoing.

Figure 5A:
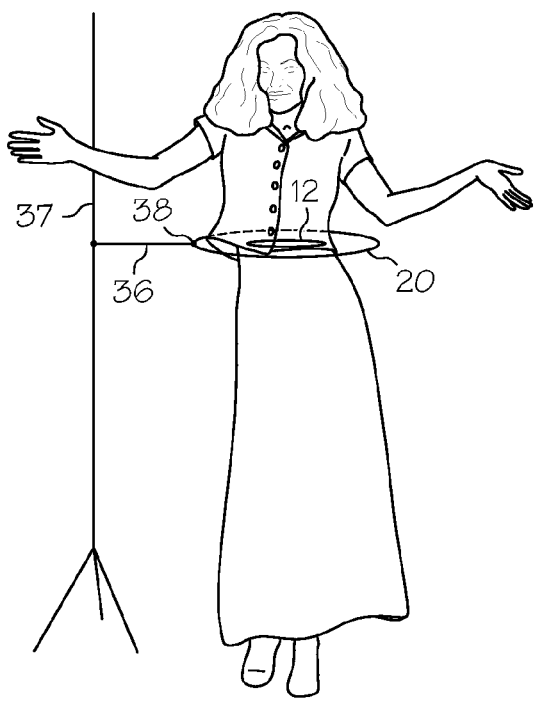
FIG. 5A is a schematic diagram depicting a coil holder for positioning the outer coil relative to the inner coil, in accordance with at least one embodiment of the present invention.

In order to adjust the external coil to produce a maximum resonance frequency, some embodiments of the present invention include a coil holder to which the external coil is secured. Referring now to FIG. 5A, one embodiment of a coil holder for a concentric, coaxial induction embodiment is shown. The coil holder is used for orienting the external coil with the internal coil. Because the above calculations are based on the orientation between the two coils, using a coil holder can simplify the setup of the system by making stationary the external coil. As seen in FIG. 5A, the coil holder 36 can simply be an arm moveably engaged to a vertical mount 37. It is important that the coil holder 36 can be raised and lowered vertically. It is also important that the coil holder 36 can be tilted, for example about a point 38 on the coil holder. In this manner, the external coil 20 can be placed concentrically and coaxially about the internal coil 12 within the patient. There are numerous other possible embodiments of the coil holder.

Figure 5B:
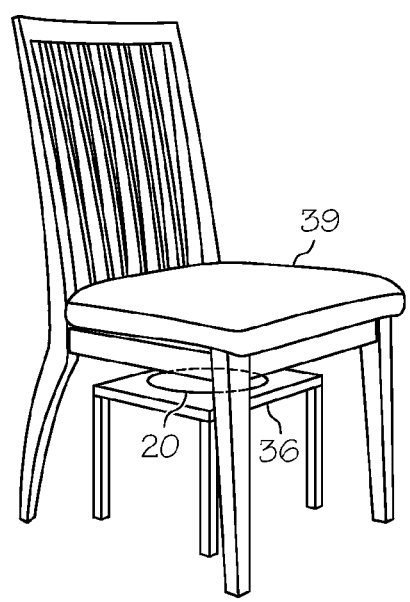
FIG. 5B is a schematic diagram depicting a coil holder for positioning the outer coil relative to the inner coil, in accordance with at least one embodiment of the present invention.

Referring now to FIG. 5B, another embodiment of a coil holder is shown. Specifically, FIG. 5B depicts a coil holder for a non-concentric, coaxial induction embodiment. As seen in FIG. 5B, the coil holder 36 can simply be a small table-like device placed under the seat of a chair 39. It is important that the coil holder 36 can be tilted, as before, thereby allowing the external coil 20 to be aligned with the internal coil within the patient to align. In such an embodiment, the patient sits down on a chair 39 and the coil holder 36 underneath the chair is oriented until the resonant frequency is achieved. There are numerous other possible embodiments of the coil holder. In some embodiments, the coil may be placed above the patient, rather than underneath (not depicted).

Figure 6:
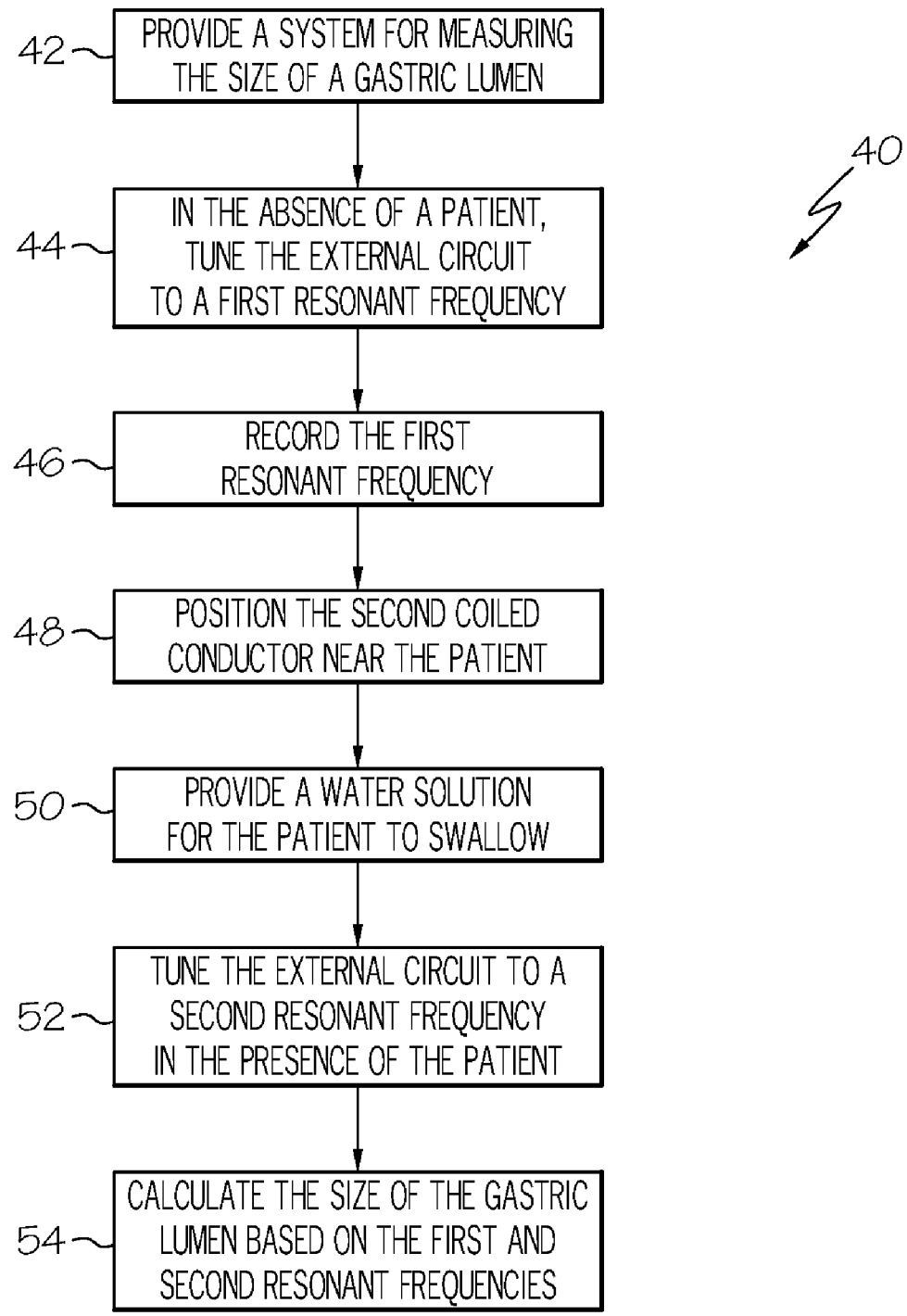
FIG. 6 is a block diagram depicting a method of measuring the size of a gastric lumen, in accordance with at least one embodiment of the present invention.

Referring now to FIG. 6, a method 40 of measuring the size of a gastric lumen is shown, in accordance with at least one embodiment of the present invention. The method 40 includes the step 42 of providing a system for measuring the size of a gastric lumen. Embodiments of such a system are described above. The method further includes the step 44 of tuning the circuit external to the banding device to a first resonant frequency in the absence of a patient. This allows the practitioner to tune and measure the circuit without the effects of the coil in the LAGB. The first resonant frequency measured is recorded in step 46 of the method. The method further includes the step 48 of positioning the external coil near the patient. As described above, the external coil can be placed near the patient in two ways: concentrically and coaxially, and non-concentrically and coaxially. The coil is either placed around the patient at the approximate level of the modified gastric band, or underneath the patient. The method further includes the step 50 of providing a water solution for the patient to swallow. The area of the lumen is based on the spike that occurs in the resonant frequency after the patient has swallowed the water solution. The water solution can be water with a solution of non-toxic paramagnetic material such as magnetic resonance imaging (MRI) contrast material. In some embodiments, the water solution can simply be water. In many cases, the method is sensitive enough to detect the gastric lumen size without ingesting of the MRI contrast material or with a very dilute concentration. The method further includes the step 52 of tuning the circuit external to the banding device to a second resonant frequency in the presence of the patient. In some embodiments of the method, the external coil can moved so as to obtain the greatest change in resonance frequency of the external circuit. For example, the external coil can be moved up and down, side to side, and can be tilted so that it is aligned with the internal coil. Finally, the method includes the step 54 of calculating the size of the gastric lumen based on the difference between the first resonant frequency and the second resonant frequency. From the change of resonance frequency of the external tuned circuit, the area of the gastric lumen is calculated, knowing the magnetic susceptibility of the MRI contrast material.

Referring now to FIGS. 7-10, a setup and method of equipment verification using a gastric magnetic susceptibility phantom. FIG. 7A depicts a top view of the basic setup of the phantom for equipment verification. The setup 60 includes a peristaltic pump 62 with longitudinal axis 63 (shown in FIG. 7B), with a lumen 64, tissue 66, and three test laparoscopically adjustable gastric bands 68. It should be noted that more test lap bands 68 could be used, depending on the accuracy desired.

Figure 7A:
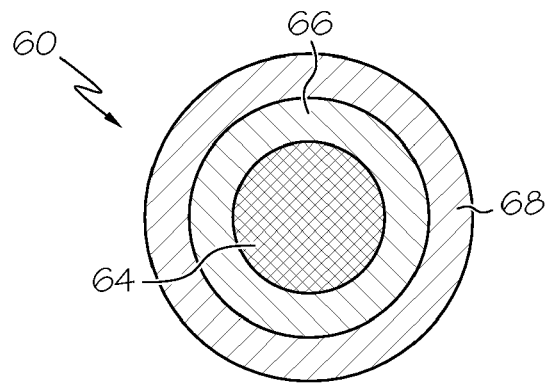
FIG. 7A is a top view of an apparatus for determining the size of a gastric lumen using a gastric magnetic susceptibility phantom, in accordance with at least one embodiment of the present invention.
Figure 7B:
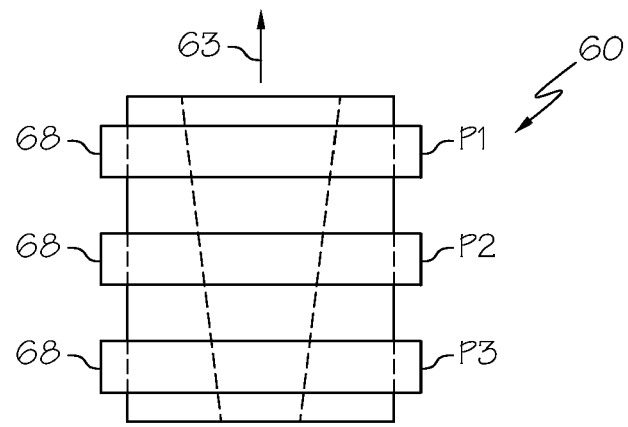
FIG. 7B is a side view of the apparatus depicted in FIG. 7A.

The peristaltic pump is filled with a magnetic contrast material and the pump is set to a speed consistent with the speed of human swallowing. As shown in FIG. 7B, a side view of the embodiment shown in FIG. 7A, the test laparoscopically adjustable gastric bands are positioned about the pump 60 at three positions, P1, P2, and P3. The first, second, and third banding devices are offset from one another along the longitudinal axis 63 of the pump.

Figure 8:
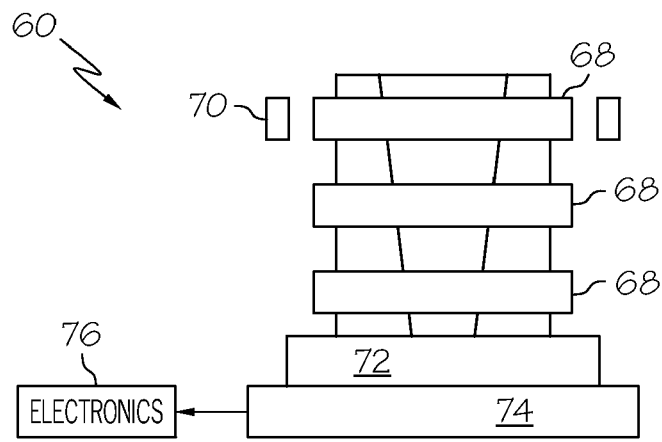
FIG. 8 is a cross sectional view of an apparatus for determining the size of a gastric lumen using a gastric magnetic susceptibility phantom, in accordance with at least one embodiment of the present invention.

Referring now to FIG. 8, the adjustable outer coil 70 is moved such that it is positioned about the test lap bands 68. The resonance frequency of each of the test lap bands 68 positioned about the pump is measured. The resonance frequencies are measured while the magnetic material passes through the phantom into the receptor 72 and back through the pump again. The values of the resonance frequencies are detected by the pickup coil 74 and transmitted to external electronics 76 for further calculations. The maximum deviation of the resonance frequency is determined from a spectrum analyzer.

Figure 9:
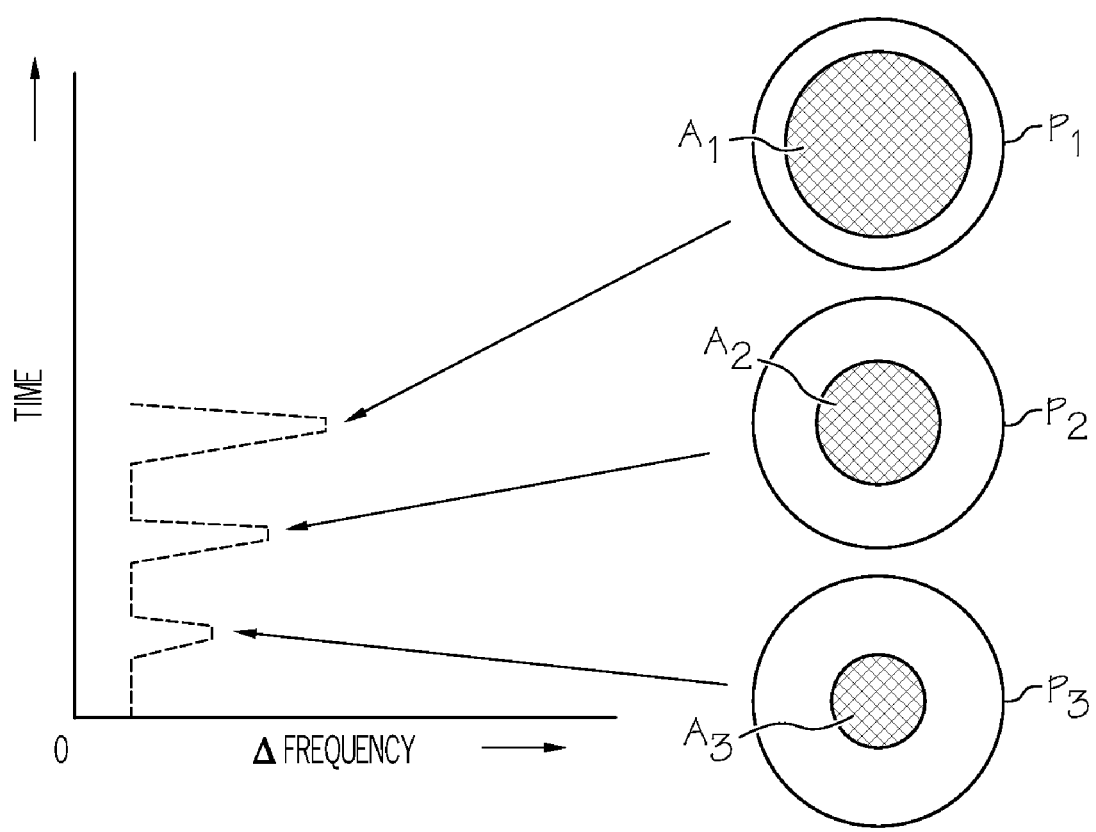
FIG. 9 is a graphical representation showing the correlation between the change in frequency and time with the area of the laparoscopically adjustable gastric band, in accordance with at least one embodiment of the present invention.

The above technique does not give an image of the gastric lumen. However, the data collected can be displayed graphically, as shown in FIG. 9. As seen in FIG. 9, the change in frequency can be graphically correlated to the areas $A_1$, $A_2$, and $A_3$ of the lap bands placed at positions P1, P2, and P3, respectively. As such, a practitioner can be assured that the external coil is working properly by comparing known good values of the $A_1$, $A_2$, and $A_3$ versus the values that were measured during the verification procedure.

It should be noted that the external frequency generating apparatus described earlier can be modified to scan across the gastric lumen using appropriate radiofrequency excitation, thereby mimicking a rudimentary flow sensing magnetic resonance imaging apparatus. Such an apparatus would provide an image, using appropriate frequency domain software.

Figure 10:
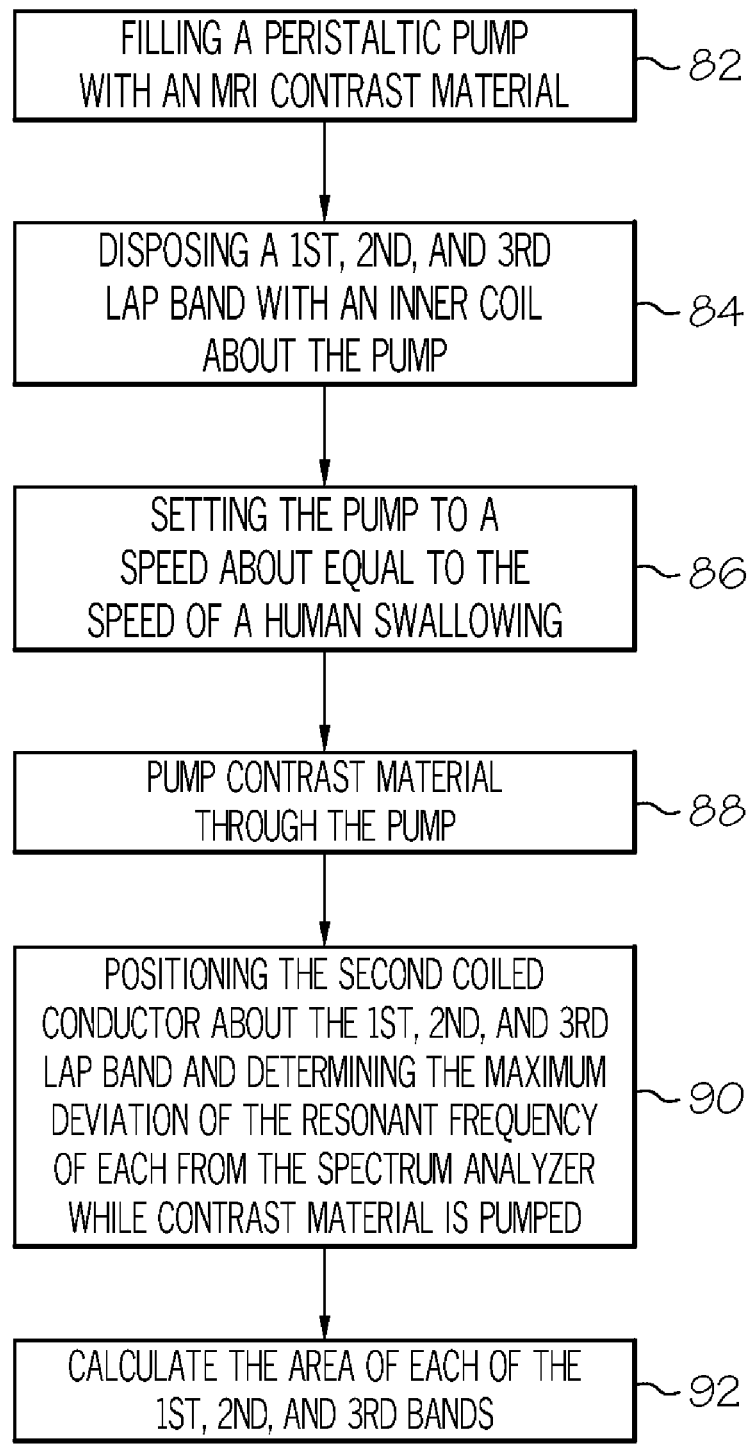
FIG. 10 is a block diagram depicting a method of measuring the size of a gastric lumen, in accordance with at least one embodiment of the present invention

The method of determining the size of a gastric lumen using a gastric magnetic susceptibility phantom is shown in FIG. 10. The method 80 includes the step 82 of filling a peristaltic pump with water or a water solution containing a magnetic resonance imaging contrast material. The method further includes the step 84 of disposing a first, second, and third gastric banding devices, as described earlier with an internal coil, about the peristaltic pump. The first, second, and third banding devices are offset from one another along the longitudinal axis of the pump. The method further includes the step 86 of setting the pump to a speed approximately equal to the speed of human swallowing. The method further includes the step 88 of pumping the contrast material through the pump. The method further includes the step 90 of positioning the external coil 70 of FIG. 8 about the first, second, and third banding devices in turn and determining the maximum deviation of the resonant frequency of the each of the first, second, and third banding device from the spectrum analyzer while contrast material is pumped through the pump. The method further includes the step 92 of calculating the area of each of the first, second, and third bands based on their resonant frequencies.

It should be noted that the steps in the method described in FIG. 10 need not be performed in the order shown, and as such, the method should not be limited to a particular order. Rather, a person of ordinary skill in the art will recognize that the method will perform equally well if, for example, the pump is set to a certain speed prior to filling it with the water solution.

Figure 11:
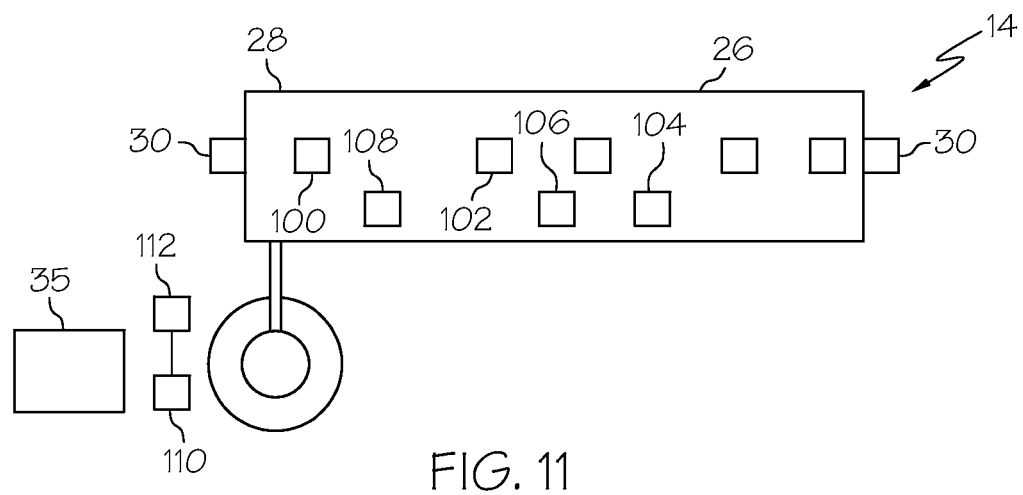
FIG. 11 is a schematic diagram of a laparoscopically adjustable gastric band with an internal coil, in accordance with at least one embodiment of the present invention.

Referring now to FIGS. 11-14, a system for measuring the size of a gastric lumen is illustrated in accordance with at least one embodiment of the present invention. FIG. 11 is similar to FIG. 3. However, instead of an internal coil, the embodiment depicted in FIG. 11 has two ultrasonic modules placed in the lap band that allow the system to measure the size and composition of the gastric lumen using time of flight ultrasound technology.

The time between transmission of the ultrasonic pulse and reception of the echo is given by:

$$t = 2 \cdot d/U, \quad (52)$$

or $$d = U \cdot t/2, \quad (53)$$

where U is the speed of sound in the medium, typically water, and d is the diameter of the lumen.

If the speed of sound is known, a dimension can be computed from the time between transmission and reception. If transmission occurs in two orthogonal directions, two dimensions of the lumen can be determined, and thus the area of the lumen can be computed. Assuming the lumen is an ellipse, the equation for the area of an ellipse using the major (a) and minor (b) axes is as follows:

$$A = \pi \cdot a \cdot b = (\pi \cdot U^2 \cdot t_1 \cdot t_2)/16 \quad (54)$$

The lumen is differentiated from the gastric tissue by instructing the patient to drink water, thus flushing the gastric area. If the lumen is clear, a clear echo signal is obtained and the time of flight of the ultrasound pulse is obtained in the clear area to determine lumen area.

To detect the presence of persistent solid mater in the gastric lumen, two methods are used. First, the orthogonal signal, that is the amplitude of the scattered ultrasonic pulse in the orthogonal direction, is compared with the original pulse echo return. And second, the amount of false return in the original pulse echo may even determine the ratio of solid to liquid matter in the cross section of the lumen encompassed by the LAGB.

Referring now to FIG. 11, the band 14 includes two orthogonal ultrasonic transmitter/receiver ("transceiver") modules 100, 102. Transceiver 100 is an anterior/posterior (a/p) ultrasonic module, and transceiver 102 is a lateral ultrasonic module.

The band 14 further includes a microprocessor 104 that measures the time of flight from each transceiver module. The microprocessor is capable of distinguishing between tissue echoes and the empty gastric lumen. The microprocessor is also capable of preparing a signal for transmission. The microprocessor is in electrical communication with a computer 105. In some embodiments, the computer and the microprocessor are incorporated into the same component. In at least one embodiment, the computer may be a look up table, capable of determining the semi-major axis, the semi-minor axis, and the scatter associated with the lumen.

The band 14 also includes a transmitter 106 capable of transmitting the signals from the band to a location outside of the body. The transmitter 106 can include an antenna for transmission, or an antenna in the band (not shown) can be in electrical communication with the transmitter.

The band 14 also includes a module 108 either containing a battery or capable of powering the laparoscopically adjustable gastric band electronics inductively.

External to the patient is an antenna 110 for receiving the transmitted signals and a receiver 112 in operative communication with the antenna. As before, a computer 35 may be included that has software capable of decoding and processing the signals transmitted by the transmitter 106 and received by the receiver 1 12. The computer software is capable of measuring the time of flight of horizontal and vertical ultrasonic pulses to determine the length and width of the gastric lumen, and combining the length and width to find the area of the gastric lumen. It should be noted that from the scatter of the horizontal into the vertical receiver and the scatter of the vertical into the horizontal receiver, the material in the gastric lumen can be determined.

Figure 12:
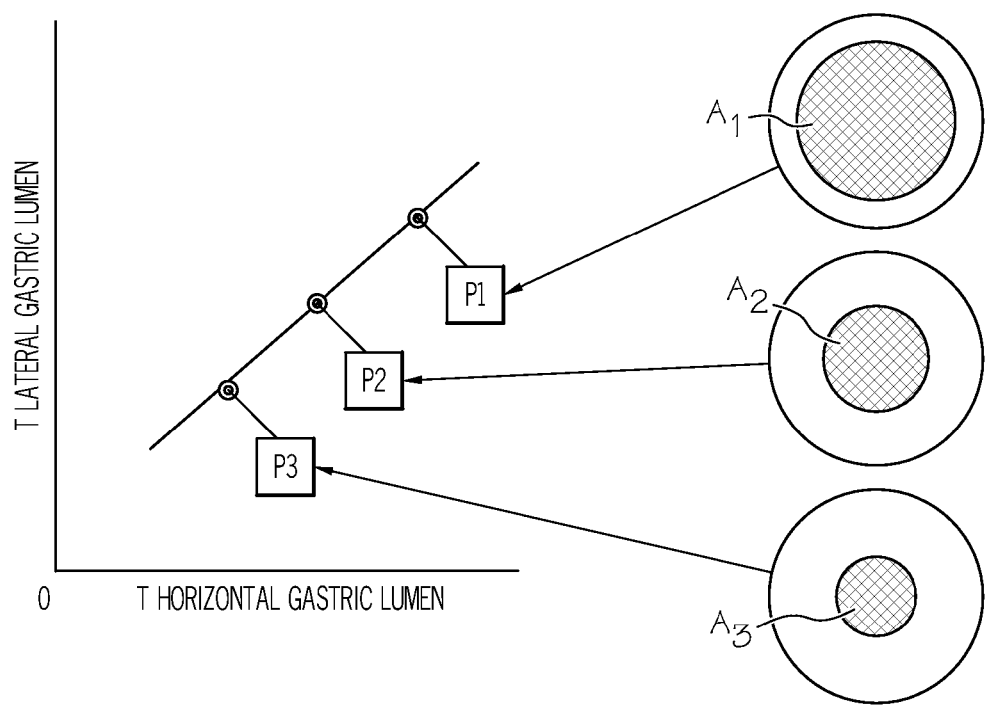
FIG. 12 is a graphical representation showing the correlation between the lateral and horizontal times of flight with the area of the laparoscopically adjustable gastric band, in accordance with at least one embodiment of the present invention.

The ultrasonic system can be calibrated in a manner similar to that described above with regards to FIGS. 7 and 8. The above technique does not give an image of the gastric lumen. However, the data collected can be displayed in a graphical manner, as shown in FIG. 12. As seen in FIG. 12, the lateral and horizontal times of flight can be graphically correlated to the areas $A_1$, $A_2$, and $A_3$ of the lap bands placed at positions P1, P2, and P3, respectively.

In some embodiments, the banding device has an inner side and an outer side where the inner side being closer to the gastric lumen than the outer side, the two ultrasonic modules being positioned on the outer side of the banding device, as in FIG. 11.

Figure 13:
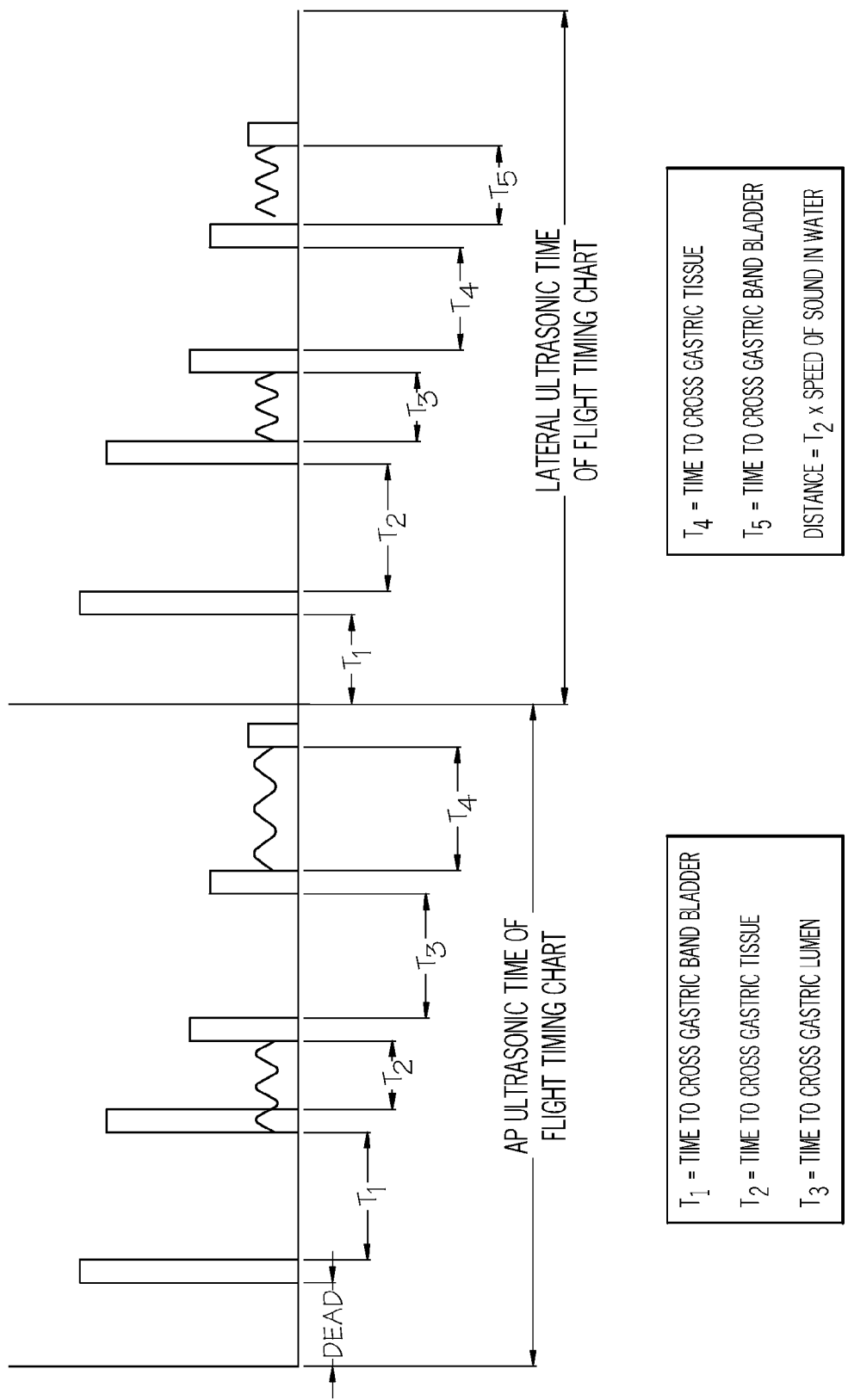
FIG. 13 is a graphical representation depicting times of flight using ultrasonic modules.

FIG. 13 depicts a pulse timing diagram depicting the time of flight using ultrasonic modules. As seen in FIG. 13, the time of flight can be determined based on the time to cross the gastric band bladder, the time to cross the gastric tissue, and the time to cross the gastric lumen.

Figure 14:
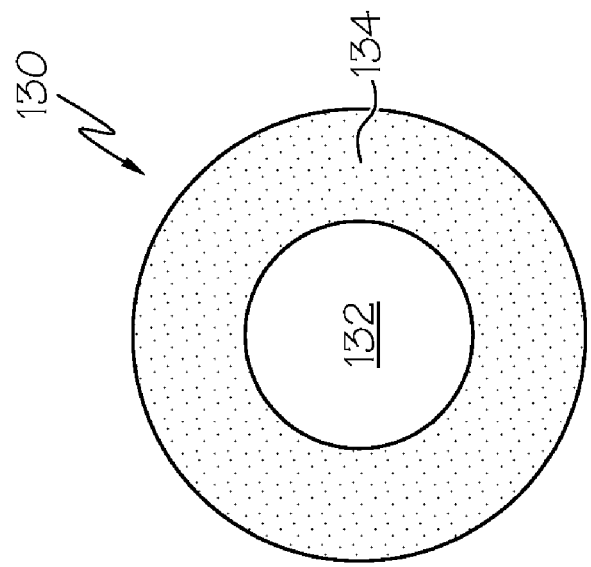
FIG. 14 is a graphical representation of data depicting the differences between induction and ultrasonic systems for measuring the size of a gastric lumen, in accordance with embodiments of the present invention.
Figure 14:
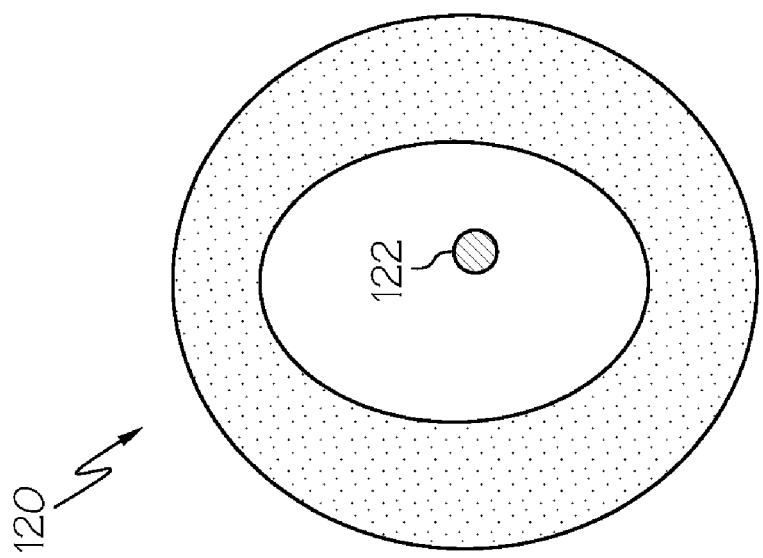

FIG. 14 is a graphically representation of the data collected for both the ultrasonic embodiment 120 and the induction embodiment 130. The ultrasonic embodiment 120 is able to detect any solid mass 122 within the lumen. In the induction embodiment 130, the area 132 from the induction embodiment is depicted as well as the area 134 from the adjustable gastric band tab circumference minus the area from the induction area.

Some embodiments of the present invention relate to luminal dimensions assessments in humans, as well as in inanimate conduits or devices.

The above disclosure is intended to be illustrative and not exhaustive. This description will suggest many variations and alternatives to one of ordinary skill in this art. The various elements shown in the individual figures and described above may be combined or modified for combination as desired. All these alternatives and variations are intended to be included within the scope of the claims where the term "comprising" means "including, but not limited to".

Further, the particular features presented in the dependent claims can be combined with each other in other manners within the scope of the invention such that the invention should be recognized as also specifically directed to other embodiments having any other possible combination of the features of the dependent claims. For instance, for purposes of claim publication, any dependent claim which follows should be taken as alternatively written in a multiple dependent form from all prior claims which possess all antecedents referenced in such dependent claim if such multiple dependent format is an accepted format within the jurisdiction (e.g. each claim depending directly from claim 1 should be alternatively taken as depending from all previous claims). In jurisdictions where multiple dependent claim formats are restricted, the following dependent claims should each be also taken as alternatively written in each singly dependent claim format which creates a dependency from a prior antecedent-possessing claim other than the specific claim listed in such dependent claim below.

This completes the description of the invention. Those skilled in the art may recognize other equivalents to the specific embodiment described herein which equivalents are intended to be encompassed by the claims attached hereto.

What is claimed is:

1. A system for measuring a size of a gastric lumen of a patient, the system comprising:
 a circuit external to a gastric banding device and to the patient, the circuit comprising a first coiled conductor, a tunable frequency generator, and a spectrum analyzer, wherein the circuit is tunable to allow a resonant frequency, wherein the frequency generator generates a current in the first coiled conductor, wherein the size of the gastric lumen is determined by a change in resonant frequencies measured by the spectrum analyzer in the first coiled conductor when in the presence of a second coiled conductor in the gastric banding device, and and wherein the size of the gastric lumen is determined without modifying the gastric banding device.

2. The system of claim 1, further comprising the gastric banding device, wherein the banding device has an inner side and an outer side, the inner side being closer to the gastric lumen than the outer side, the second coiled conductor being positioned on the inner side.

3. The system of claim 1, further comprising a heating control element, the heating control element being in electrical communication with the second coiled conductor.

4. The system of claim 1, further comprising at least one coil holder for orienting the first coiled conductor with the first coiled conductor.

5. The system of claim 1, wherein the size of the gastric lumen is determined by a change in resonant frequencies measured by the spectrum analyzer in the first coiled conductor when in the presence of a second coiled conductor in the gastric banding device and after the patient has swallowed a liquid.

6. The system of claim 5, wherein the liquid is a paramagnetic solution.

7. A system for measuring a size of a gastric lumen, the system comprising:
- a circuit external to a gastric banding device, the circuit comprising a first coiled conductor, a tunable frequency generator, and a spectrum analyzer,
- wherein the circuit is tunable to allow a resonant frequency,
- wherein the frequency generator generates a current in the first coiled conductor, and
- wherein the spectrum analyzer measures resonant frequency values in the first coiled conductor; and
- a computer comprising a computer-readable storage medium comprising instructions that, when executed, cause the computer to:
- calculate the size of the gastric lumen based on the difference between a first resonant frequency value of the first coiled conductor and a second resonant frequency value of the first coiled conductor when in the presence of a second coiled conductor in the gastric banding device.

8. The system of claim 7, further comprising the gastric banding device.

9. The system of claim 7, wherein the frequency generator is a variable frequency oscillator.

10. The system of claim 7, wherein the instructions that cause the computer to calculate the size of the gastric lumen based on the difference between a first resonant frequency value of the first coiled conductor and a second resonant frequency value of the first coiled conductor when in the presence of a second coiled conductor in the gastric banding device comprise instructions that cause the computer to:
- calculate the size of the gastric lumen based on the difference between a square of the first resonant frequency value of the first coiled conductor and a square of the second resonant frequency value of the first coiled conductor when in the presence of a second coiled conductor in the gastric banding device.

11. The system of claim 7, wherein the instructions that cause the computer to calculate the size of the gastric lumen based on the difference between a first resonant frequency value of the first coiled conductor and a second resonant frequency value of the first coiled conductor when in the presence of a second coiled conductor in the gastric banding device comprise instructions that cause the computer to:
- calculate the size of the gastric lumen based on a change in a bandwidth of the first resonant frequency value and the second resonant frequency value.

\* \* \* \* \*